(12) United States Patent
Bos et al.

(10) Patent No.: US 9,339,514 B2
(45) Date of Patent: *May 17, 2016

(54) METHOD FOR TREATING GLAUCOMA

(71) Applicant: APTISSEN SA, Plan-les-Ouates (CH)

(72) Inventors: Gilles Bos, Petit-Lancy (CH); Philippe Sourdille, Liniers (FR)

(73) Assignee: APTISSEN SA, Plan les Ouates (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/248,627

(22) Filed: Apr. 9, 2014

(65) Prior Publication Data

US 2014/0221972 A1    Aug. 7, 2014

Related U.S. Application Data

(63) Continuation-in-part of application No. 12/557,832, filed on Sep. 11, 2009, now Pat. No. 8,715,266.

(60) Provisional application No. 61/096,654, filed on Sep. 12, 2008.

(51) Int. Cl.
*A61F 9/007*     (2006.01)
*A61K 31/728*    (2006.01)
*A61K 9/00*      (2006.01)
*A61K 9/06*      (2006.01)

(52) U.S. Cl.
CPC .............. *A61K 31/728* (2013.01); *A61K 9/0051* (2013.01); *A61F 9/00781* (2013.01); *A61K 9/06* (2013.01)

(58) Field of Classification Search
None
See application file for complete search history.

(56) References Cited

U.S. PATENT DOCUMENTS

2007/0196426 A1      8/2007  Hermitte et al.
2008/0058760 A1*     3/2008  Agerup ..................... 604/521
2009/0081277 A1*     3/2009  Robinson et al. ............. 424/428

* cited by examiner

*Primary Examiner* — H. Sarah Park
(74) *Attorney, Agent, or Firm* — Sofer & Haroun, LLP

(57) ABSTRACT

A method of treating glaucoma or other eye disease in a patient is provided. The method includes injecting an eye of the patient with a cohesive monophasic gel containing cross-linked hyaluronic acid or its salt. The injection can be under the scleral flap and/or conjunctiva of the eye, thereby creating and maintaining a conjunctival bleb, and/or the injection can be in the supra-scleral and/or supra-choroidal (sub-scleral) space of the eye thereby reducing the intraocular pressure.

16 Claims, 7 Drawing Sheets

METHOD FOR TREATING GLAUCOMA

BACKGROUND OF THE INVENTION

1. Field of the Invention

A gel facilitates perforating and non-perforating glaucoma surgery.

2. Description of the Related Art

Glaucoma is a group of eye diseases that gradually steal sight without warning. In the early stages of the disease, there may be no symptoms. Experts estimate that half of the people affected by glaucoma may not know they have it.

There is no cure for glaucoma. However, medication or surgery can slow or prevent further vision loss. The appropriate treatment depends upon the type of glaucoma among other factors.

Primary open angle glaucoma is the most common form of glaucoma. It happens when the eye's drainage canals become clogged over time. The inner eye pressure (also called intraocular pressure or IOP) rises because the correct amount of fluid can't drain out of the eye. With open angle glaucoma, the entrances to the drainage canals are clear and should be working correctly. The clogging problem occurs further inside the drainage canals, similar to a clogged pipe below the drain in a sink. Most people have no symptoms and no early warning signs. If open angle glaucoma is not diagnosed and treated, it can cause a gradual loss of vision. This type of glaucoma develops slowly and sometimes without noticeable sight loss for many years. It usually responds well to medication, especially if caught early and treated.

Angle closure glaucoma is also known as acute glaucoma or narrow angle glaucoma. It is much more rare and is very different from open angle glaucoma in that the eye pressure usually rises very quickly. This happens when the drainage canals get blocked or covered over, like a sink with something covering the drain. With angle closure glaucoma, the iris is not as wide and open as it should be. The outer edge of the iris bunches up over the drainage canals, when the pupil enlarges too much or too quickly. This can happen when entering a dark room.

Treatment of angle closure glaucoma usually involves surgery to remove a small portion of the outer edge of the iris. This helps unblock the drainage canals so that the extra fluid can drain. Symptoms of angle closure glaucoma may include headaches, eye pain, nausea, rainbows around lights at night, and very blurred vision.

Secondary glaucoma can occur as the result of an eye injury, inflammation, tumor or in advanced cases of cataract or diabetes. It can also be caused by certain drugs such as steroids. This form of glaucoma may be mild or severe. The type of treatment will depend on whether it is open angle or angle closure glaucoma.

The success of glaucoma surgery depends on the modification of wound healing. The aim is to limit a healing process and to avoid fibrous tissue formation that are natural biologic responses and are indispensable for all other surgical procedures. Risk factors include age, race, type of glaucoma, conjunctival inflammation and aphakia.

FIG. 1 shows the process of wound healing in glaucoma filtering processes.

As shown in FIG. 1, the stages of wound healing include injury, inflammation, coagulation (clot formation), cellular migration and proliferation, angiogenesis, and scar formation. There are phenomena associated with each stage. For example, inflammation includes vascular permeability, cellular infiltration, plasma proteins, fibrinogen, fibronectin, platelets and cellular procoagulant. Cellular migration and proliferation is associated with fibroblasts, neurophils, macrophages, monocytes and epithelial cells. Scar formation is associated with collagen formation and cross linking.

The strategies to interfere with the process of wound healing after glaucoma surgery include meticulous surgical technique to minimize trauma to the conjunctiva, episclera and iris to decrease leakage of plasma proteins. Other strategies interfere with the process of wound healing at the different stages shown in FIG. 1.

Treatment at the inflammation stage include non-steroidal anti-inflammation drugs (NSAIDs), including aspirin, indomethacin, fluiboprofen. Steroidal drugs used at the inflammation stage can include prednisolon, fluoromethalon and dextramethssone.

Treatment at the coagulation (clot formation) stage can include thrombolytic drugs, urokinase, streptokinase and t-PA. Treatment at the cellular migration stage can include mitomicine C and 5 FU. Treatment at the scar formation stage includes Beta-aminopropionitrile, D-penicillamine and colchicine.

However, there is a continuing need for treatments that will increase the likelihood of a successful outcome from eye surgery, especially glaucoma surgery.

SUMMARY OF THE INVENTION

It is therefore an object of the invention to overcome one or more disadvantages associated with the related art.

The invention, in part, pertains to a method of treating glaucoma or other eye disease that includes injecting an eye of a patient with viscoelastic material made of a cross-linked high water content (hydrogel) biocompatible gel of hyaluronic acid (HA) or its salt, preferably sodium hyaluronate in the form of a monophasic gel. The cross-linking agent can be 4-butanediol diglycidylether. The monophasic gel can contain about 2.25% (w/w) of the salt of hyaluronic acid, and the cross linking rate can be about 0.5-50%. Injection can be under a scleral flap or under conjunctiva. The method can be perforating or non perforating surgery such as trabeculectomy, visocanalostomy or deep sclerectomy.

The method can be a trabeculectomy that includes applying peribulbar anesthesia, dissecting the conjunctiva, dissecting a scleral flap, performing an opening to the Anterior chamber of the eye, performing an iridectomy, creating an opening in the scleral bed (at the fornix side of the scleral bed), injecting the cross-linked sodium hyaluronate gel through the opening in the supra-choroidal (sub-sclera)-space, suturing the scleral flap, injecting the gel under the scleral flap, injecting the gel under the conjunctiva, and suturing the conjunctiva The method can be a viscocanalostomy that includes applying peribulbar or topical anesthesia, dissecting the conjunctiva, dissecting a first scleral flap at a site with at least one apparent collecting channel, dissecting a second scleral flap close to a ciliary body, creating a Trabeculo-Descemet-Membrane window, unroofing Schlemms' canal, excising the second sclera flap, inserting a canula into two ostia of the Schlemms' canal, repeatedly injecting a gel into the two ostia, creating an opening in a sclera bed (preferably at the fornix side of the scleral bed), injecting the cross-linked hyaluronic acid or its salt gel through the opening in the supra-choroidal (sub-scleral) space, suturing the first scleral flap, injecting the cross-linked hyaluronic acid or its salt gel below the first scleral flap, injecting the gel under the conjunctiva to create a large conjunctival bleb, and suturing the conjunctiva.

The method can be a deep sclerectomy that includes applying peribulbar or topical anesthesia, dissecting the conjunctiva, dissecting a first scleral flapat a site with at least one apparent collecting channel, dissecting a second sclera flap close to a ciliary body, creating a Trabeculo-Descemet-Membrane window, unroofing a Schlemm's canal, excising the second sclera flap, creating an opening preferably at the fornix side of the scleral bed, injecting the cross-linked hyaluronic acid or its salt gel through the opening in the suprachoroidal (sub-scleral) space, suturing the first sclera flap, injecting the gel below the first scleral flap, injecting the gel under the conjunctiva to create a large conjunctival bleb, and suturing the conjunctiva.

The invention, in part, pertains to a composition for application during eye surgery that can include a cross linked high water content (hydrogel) biocompatible viscoelastic gel, and a pharmacologically acceptable carrier.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention. The drawings illustrate embodiments of the invention and together with the description serve to explain the principles of the embodiments of the invention.

FIG. 3 is a comparison of phases, where

DETAILED DESCRIPTION OF THE INVENTION

Figure 1:
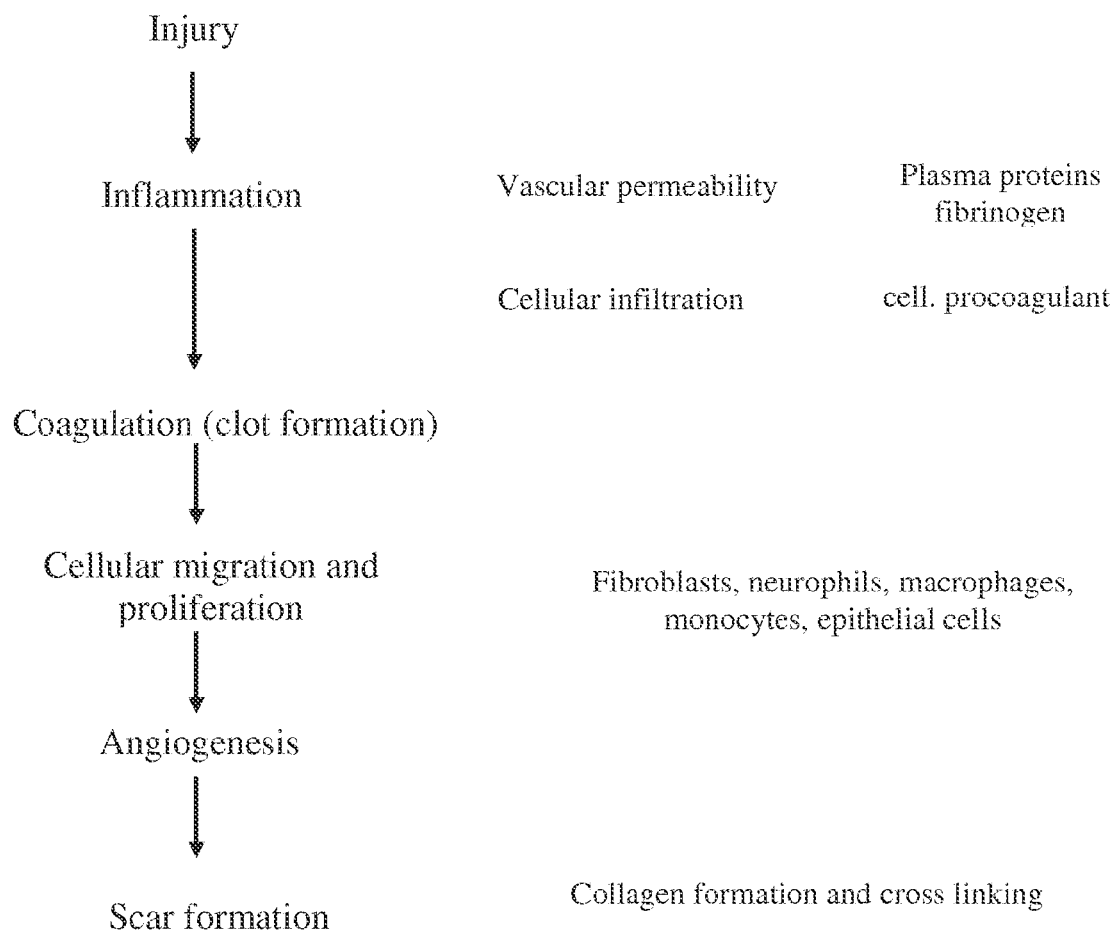
FIG. 1 shows the stages of wound healing.

Advantages of the present invention will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Glaucoma is a progressive disease characterized by an optic neuropathy that will induce characteristic visual field defects. The main risk factor for glaucoma is high intraocular pressure (IOP) however other risk factors have been recognized.

Today the only evidence based treatment for glaucoma is lowering of the IOP. The first choice is in the majority of cases medical therapy. If despite maximal medical therapy the disease progresses, laser therapy or surgery is advocated.

Trabeculectomy is the most frequent surgical procedure chosen by the surgeons. It is a perforating filtering procedure that creates a fistula between the anterior chamber and the sub-conjunctival space. Trabeculectomy however has a number of potentially serious side effects: athalamy, hypotony, choroid effusion, endophthalmitis. The success rate of this procedure depends on the permeability of the fistula and the presence of a filtering conjunctival bleb.

Scarring of the tissues is the most frequent cause of failure, and substances have been introduced to influence the rate of fibrosis at the surgical site. MMC and 5FU, two anti-mitotic drugs, are used by application on the sclera and under the conjunctiva to inhibit fibroblasts and vascular endothelium proliferation. Unfortunately, these substances may lead to severe complications with sight-threatening consequences.

In order to avoid operatives and post-operatives complications seen with trabeculectomy, other, non-perforating procedures have been introduced. Implants used until now have been made of collagen or cross-linked HA (product SKGEL from Corneal). Those products are solid implant that do not adapt to the cavity shapes, and cannot be injected under the conjunctiva (because they are not gels but solids). In Deep Sclerectomy (DS) with or without solid implant and Viscocanalostomy (VCS) a large descemetic window is created and the Schlemm's canal (SC) is cleaned with abrasion of the juxta-canalicular tissue. This allows the aqueous humor to percolate through the very thin descemetic membrane and Schlemm's canal, to collect in the deep scleral bed and to be evacuated either via the collector channels and aqueous veins or through the conjunctival filtering bleb. Viscoelastic substances are actually used to maintain the intrascleral cavity open as well as a patent conjunctival bleb. In VCS, a viscoelastic is injected into the Schlemm's canal in order to enlarge and eventually micro-perforate the later.

In one approach, the viscoelastic can be a non cross-linked hyaluronic acid. However, this substance has only a short life-time and cannot induce long-term space-maintenance.

The major reason for failure of these procedures is fibrosis either at the level of the scleral cavity or at the level of the conjunctiva.

The use of a substance that will remain for a prolonged time as space-maintainer under the scleral flap and/or the conjunctival bleb may improve the surgical success rate of penetrating and non penetrating glaucoma surgery.

A cross-linked biocompatible viscoelastic gel is thus indicated for perforating and non perforating glaucoma surgery. Injected under the scleral flap and/or the conjunctiva, it acts for a prolonged time as a space filler and a drainage device and limits the postoperative fibrosis thus improving the surgical success rate. Its gel texture, capable to adapt to any cavity shape and to fill the whole space, creates a biocompatible neighborhood that avoids cell proliferation and differentiation into fibrous tissue. In a preferred embodiment, its slowly resorbable property increases its tolerance and non-immunogenicity and leads to the non fibrous healing of the sclera or conjunctival tissue. This preserves the regeneration of specialized and functional cells and maintains an efficient uveoscleral outflow of aqueous humour through tissues.

There are three fundamental characteristics of the gel injected that are needed in order to obtain a more successful surgical outcome:
1. The product has to drain water and not clog the surgically created canals, and thus can be made of a high water content so that it could conduct the aqueous humor flow
2. The product can be a biocompatible viscoelastic gel, in order to limit scarring formation which would induce closure of the drainage
3. The product is cross-linked in order to be stable and to maintain the above mentioned features.

In more detail, a high water content is obtained from using a hydrogel material and the injected product is prepared using an aqueous pharmacologically acceptable medium.

To obtain a biocompatible viscoelastic gel, the following is preferred:

The biocompatible viscoelastic gel is preferably made of natural polysaccharide(s) such as hyaluronic acid or its salt, chondroitin sulfate, keratan, keratan sulfate, heparin, heparin sulfate, alginate, cellulosic derivatives, chitosan, xanthan, or one of the salts thereof. Such biocompatibility avoids inflammation, foreign body reaction, or any biological signal which would increase scarring process.

The gel texture, capable to adapt to any cavity shape and to fill the whole space, creates a biocompatible neighborhood environment that would avoid cells proliferation and differentiation into fibrous scarring tissue.

In a preferred embodiment, the gel injected contains hyaluronic acid (HA), or one of the salts thereof. HA has biological properties that enhance this biocompatible characteristic and limits scarring formation.

A minimum content of polysaccharide is about 0.1% and a maximum is about 20%. For a concentration below about 0.1%, the viscoelastic behavior of HA is lost, and this means that no flexible network is obtained and thus efficacy of the cross-linking is uncertain. The biocompatibility of HA derivatives showed signs of intolerance when concentration was over about 20%.

Pharmacologically active ingredients can be added into the gel in order to further limit scarring process (antimitotic agent, anti inflammatory agent, etc).

Regarding the creation of a cross-linked network, the following should be noted:

The cross-linking agent is a bifunctional or a polyfunctional molecule, which can be at least one of epoxys (for example 1,4 butanediol diglycidylether (BDDE) or 1,2,7,8-Diepoxyoctane (DEO)), divinylsulfone (DVS) or carbodiimide (for example 1-ethyl-3-(3-dimethylaminopropyl) carbodiimide (EDC) or N-cyclohexyl-N-(4-methylmorpholinium) ethyl carbodiimide (CMC)). A preferred embodiment corresponds to the injection of a gel cross-linked with BDDE, which is reported as the less toxic agent among the above listed ones.

Cross-linking ratio w/w can be chosen between about 0.5% to about 50%. A preferred embodiment is between about 2% to about 20%. The cross-linking provides long term stability to the polysaccharide in order to maintain drainage functions. Any addition of cross-linking within the polysaccharide gel increases its stability, even at low level such as about 0.5%. Significant stabilization of several months in intradermal tissue has been described in literature with level of cross-linking between about 2 to about 20%. Beyond a certain level of cross-linking, the gel becomes a solid and is no longer injectable neither adaptable to a cavity shape. The maximum level of cross-linking also depends on the cross-linker agent.

A preferred embodiment is a monophasic gel, corresponding to an homogeneous viscoelastic cross-linked gel network Another preferred embodiment is a polydensified monophasic gel, such as is mentioned in U.S. Publication 2007/0196426 Biocompatible cross-linked gel.

Solid particles or fragments highly cross-linked can be inserted in the injected gel according to above description, in order to obtain a biphasic composition, with a biocompatible cross-linked viscoelastic polysaccharide(s) gel as the carrier.

Molecules such as polyol or antioxidant can be added to the cross-linked gel in order to enhance its stability.

An effective viscoelastic gel is formed from a salt of hyaluronic acid. Preferably the salt is a sodium salt, i.e., sodium hyaluronate. However, other counterions can be used, such as potassium, lithium, magnesium, ammonium, etch. Also, mixed salts can be used.

The salt of hyaluronic acid yields a superior viscoelastic as a monophasic, which can be attained by cross-linking. A typical cross linking agent is 4-butanediol diglycidylether. The 4-butanediol diglycidylether can be modified with glycidyl isopropyl ether.

In a preferred embodiment, the viscoelastic material is an injectable and resorbable cross-linked gel of hyaluronic acid from biofermentation origin. The gel can be presented in a 1 mL prefilled glass syringe, and sterilized by moist heat by autoclave. The viscoelastic can be a monophasic gel.

In a preferred embodiment, the viscoelastic material is a sterile, pyrogen free, colorless, transparent, viscoelastic and cohesive gel, made of cross-linked sodium hyaluronate (NaHA). The cross-linking agent, BDDE (1,4-butanediol diglycidylether), creates covalent bonds between NaHA chains (ether bonds). The NaHA concentration equals about 2.25% (w:w) and cross-linking rate, corresponding to the ratio[mass of BDDE+(mass BDDE+mass NaHA)]*equals about 5%.

The NaHA concentration is not restricted to about 2.25%, but can range from about 1.5% to about 3%. The cross-linking rate is not restricted to about 9%, but can range from about 5% to about 20%.

The hyaluronic acid of the present invention can be a natural polymer (glycosaminoglycan) composed of alternating residues of the monosaccharides D-glucuronate and N-acetyl-D-glucosamine, linked in repeating units. This polysaccharide is a constituent of all connective tissues in humans and all vertebrates. It is chemically, physically, and biologically identical in all species and has extraordinarily good biological compatibility. The cross-linking agent is also the same: 1,4-butanediol diglycidylether (BDDE), the safest of the cross-linking agents commonly used.

Figure 2:
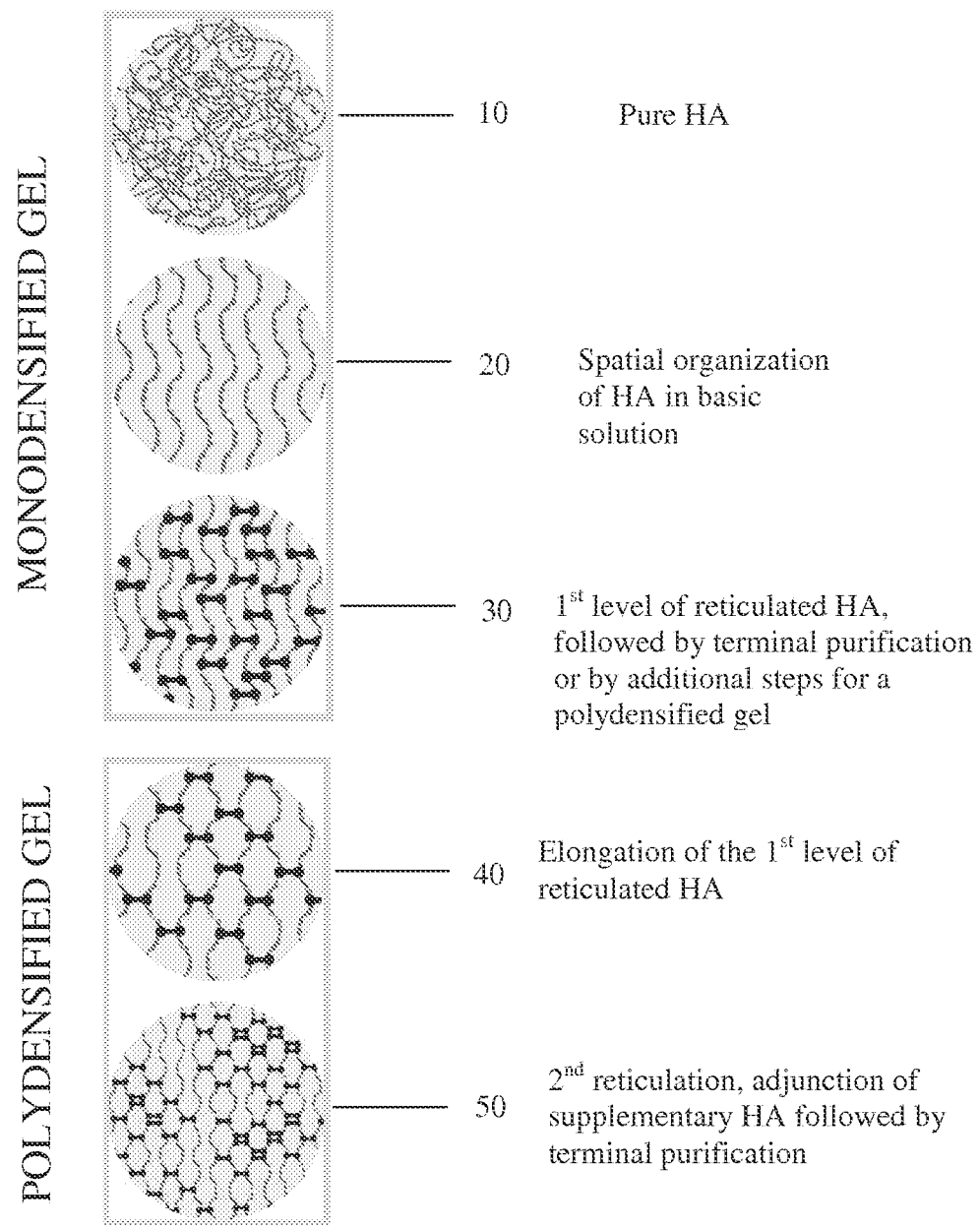
FIG. 2 shows a particular process of manufacturing of monophasic cross-linked gels of HA, monodensified (3 first steps) or polydensified (2 additional steps).

The method of manufacturing of a cross-linked monophasic gel of hyaluronic acid is typically shown in FIG. 2. The amorphous structure 10 of pure hyaluronic acid (HA) or its salt has little organization. HA can be spatially organized 20 in a basic solution and then reticulated to a first level 30, thanks to the addition of a cross-linker under appropriate conditions. This step could be followed by terminal purification in order to obtain a monophasic monodensified cross-linked gel of hyaluronic acid, or followed by additional steps in order to obtain a monophasic polydensified cross-linked gel of hyaluronic acid, according to patent application US2007/0196426. Preferably the first level of reticulated HA can be elongated 40. A second reticulation 50 can follow, with the adjunction of supplementary HA followed by terminal purification.

Figure 3A:
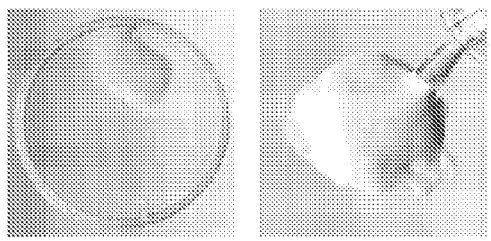
FIG. 3a shows a monophasic gel and FIG. 3b shows a biphasic gel, made of cross-linked particles in a non cross-linked gel carrier.
Figure 3B:
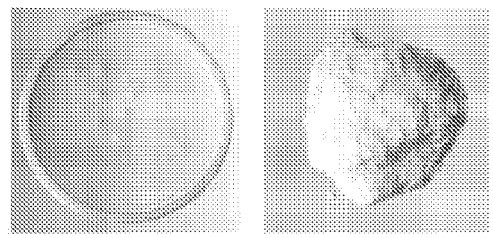

The result is a monophasic material that is shown in FIG. 3, where FIG. 3*a* shows the preferred cohesive monophasic gel compared to the dispersive biphasic material shown in FIG. 3*b*, made of cross-linked particles of HA embedded into a non cross linked gel of HA. Since this non cross-linked substance has only a short life-time and cannot induce long-term space-maintenance and since solid particles cannot fill the whole cavities, this biphasic composition cannot improve the surgical success rate of penetrating and non penetrating glaucoma surgery. Solid particles or highly cross linked fragments can be embedded into a gel of the invention in order to obtain a biphasic composition, with a biocompatible cross linked viscoelastic gel as the carrier.

Figure 4:
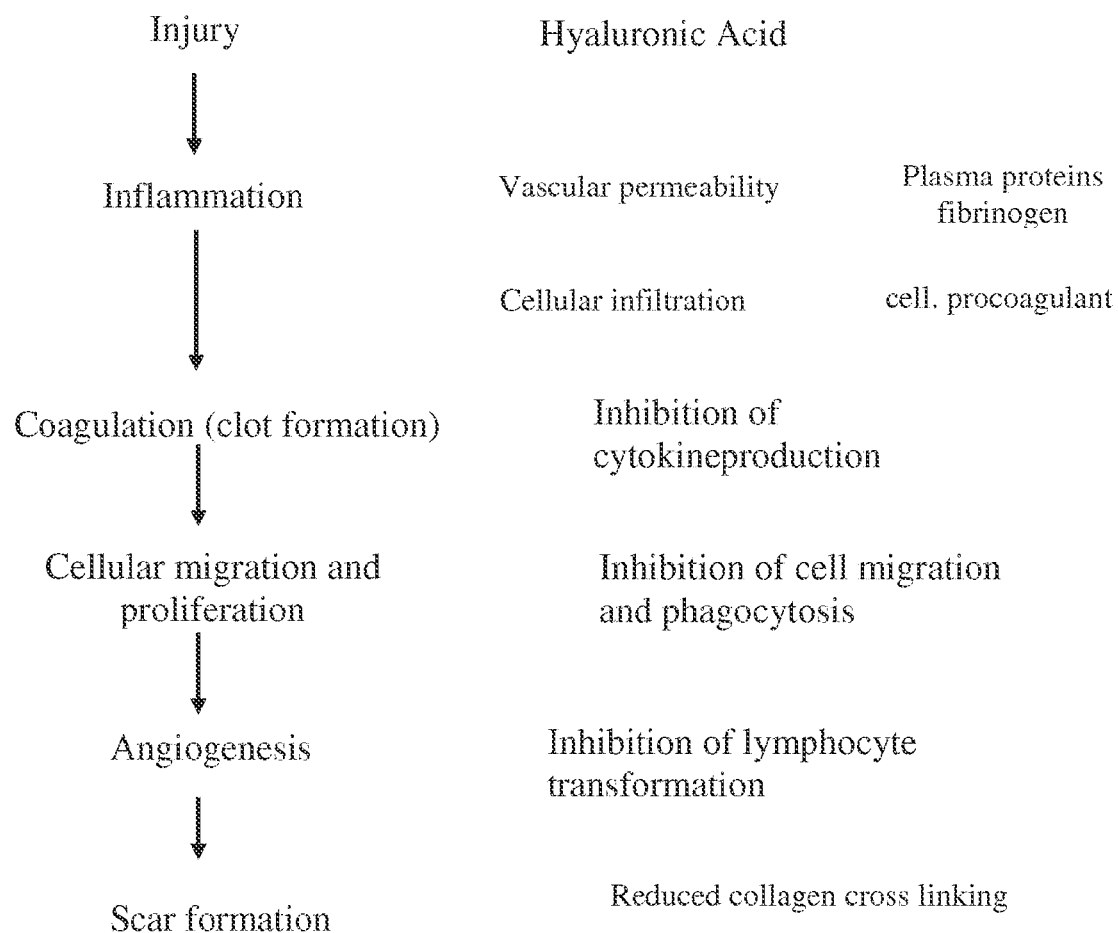
FIG. 4 shows a schematic of eye injury and therapy where hyaluronic acid of the invention is employed.

FIG. 4 shows a schematic of eye injury and therapy where the hyaluronic acid of the invention is employed. As opposed to the conventional therapy shown in FIG. 1, the utilization of the viscoelastic material made of hyaluronic acid (or one of the salts thereof) of the invention provides at least the following advantages:

Inhibition of cytokine production,
Inhibition of cell migration and phagocytosis, and
Inhibition of lymphocyte transformation.

These advantages come in addition to the biocompatible neighborhood that avoids cell proliferation and differentiation into fibrous tissue.

In practice, the viscoelastic cross-linked gel of the invention is a biocompatible hydrogel which works by being injected during the glaucoma surgery in the scleral flap, or between the sclera and the conjunctivae in order to provide a space-occupying viscoelastic supplement and to control the wound healing process. It results in a bleb keeper.

One typical application of the viscoelastic material of the invention is in a trabeculectomy. A trabeculectomy can have the following surgical procedure:

Surgical Procedure:

Anesthesia is peribulbar (Lidocaine-Adrenalin) The conjunctival flap is fornix-based. After diathermy of the scleral bed, a 4 mm*4 mm rectangular scleral flap of approximately one-half scleral depth is dissected to the limbus. If necessary a paracenthesis may be done at this stage of the surgery.

While elevating the scleral flap, a sclerectomy is done by a radial incision made immediately under the flap junction. The iris may prolapse through the wound.

A small iridotomy is performed and will allow the iris to fall back.

As a preferred step, before suturing the first scleral flap, a small incision (about 0.5 mm to 2 mm) is done in the sclera bed (preferably at the fornix end of the scleral bed) for injecting the gel comprising hyaluronic acid or its salt. The canula is inserted inside this opening, with lumen positioned between the sclera and the choroid. This injection of about 0.1-0.3 mL is performed by smooth and continuous pressure on the syringe plunger in order to spread it around the injection point. This separates the ciliary body and the choroid from sclera, to increase the pressure difference between the anterior chamber and the supra-choroidal space.

The scleral flap is then sutured with interrupted or releasable 10.0 nylon sutures. At this stage of the procedure viscoelastic material of the invention is injected under the scleral flap. Conjunctiva is closed with interrupted or continuous 10.0 nylon sutures.

The viscoelastic material of the invention is also injected under the conjunctiva in order to create a large conjunctival bleb. If necessary, BSS is injected into the anterior chamber.

Topical antibiotic and anti-inflammatory drops are prescribed postoperatively for 1 month.

Another typical application of the material of the present invention is in viscocanalostomy. A procedure for viscocanalostomy can be as follows:

Surgical Procedure:

Anesthesia is peribulbar (Lidocaine-Adrenalin) or topical (tetracain drops with subconjunctival Lidocaine-Adrenalin). The conjunctival flap is fornix-based.

To avoid damage to Schlemm's canal (SC), the collector channels and the episcleral vascular bed, diathermy is not used. Instead, hemostasis is achieved by Glypressine embedded (Ferring AG Sweden) sponge application on the surgical wound.

A site with at least one apparent collecting channel is chosen and a 5*5 mm limbal based rectangular or parabolic, thin superficial scleral flap is dissected 1.5 mm into clear cornea. A second, deep scleral flap is dissected close to the ciliary body.

When reaching SC, the latter is unroofed by gently pulling on the scleral flap and concomitantly peeling the fibrotic lining from the bottom of the canal, procedure continued into a cleavage plane, between the corneal stroma and the Descemet's membrane, creating a Trabeculo-Descemet-Membrane (TDM) window. The bottom of the canal is peeled and the juxta-canalicular tissue abraised.

As soon as the TDM window is created, percolation of the aqueous humor through the remaining peripheral Descemet's membrane and/or SC is observed. A 150 microns canula is inserted into the two ostia of the SC and the viscoelastic material of the invention is repeatedly injected inside. The deep flap is excised with micro-scissors and viscoelastic material of the invention is injected in the scleral cavity. The superficial flap is sutured with 2 separate 10-0 nylon sutures.

As a preferred step, before suturing the first scleral flap, a small incision (about 0.5 to 2.0 mm) is done in the sclera bed, preferably done at the fornix end of the scleral bed for injecting the gel comprising hyaluronic acid or its salt. The canula is inserted inside this opening, with lumen positioned between the sclera and the choroid. This injection of about 0.1-0.3 mL is performed by smooth and continuous pressure on the syringe plunger in order to spread it around the injection point. This separates the ciliary body and the choroid from sclera, to increase the pressure difference between the anterior chamber and the supra-choroidal space.

At this stage of the procedure, viscoelastic material of the invention is injected under the scleral flap. The conjunctiva is sutured using 2 separate 10-0 nylon sutures. The viscoelastic material of the invention is injected under the conjunctive in order to create a large conjunctival bleb. Topical antibiotic and anti-inflammatory drops are prescribed postoperatively for 1 month.

Another typical application of the viscoelastic material of the invention is in deep sclerectomy. A procedure for a deep sclerectomy is as follows:

Surgical Procedure:

Anesthesia is peribulbar (Lidocaine-Adrenalin) or topical (tetracain drops with subconjunctival Lidocaine-Adrenalin). The conjunctival flap is fornix-based.

After diathermy of the vascular bed a 5*5 mm limbal-based rectangular, thin superficial scleral flap is dissected 1.5 mm into clear cornea by means of a diamond knife. A second, deep scleral flap is dissected close to the ciliary body.

When reaching SC, the latter is unroofed by gently pulling on the sc flap and concomitantly peeling the fibrotic lining from the bottom of the canal, procedure continuing into a cleavage plane, between the corneal stroma and the Descemets membrane, creating a Trabeculo-Descemet-Membrane (TDM) window. The bottom of the canal is pealed and the juxta-canalicular tissue abraised. The second flap is excised. As soon as the TDM window is created, percolation of the aqueous humor through the remaining peripheral Descemet's membrane and/or SC is observed. The viscoelastic material of the invention is injected into the scleral cavity.

As a preferred step, before suturing the first scleral flap, a small incision (about 0.5 to 2.0 mm) is done in the sclera be (preferably at the fornix end of the scleral bed) for injecting the gel comprising hyaluronic acid or its salt. The canula is inserted inside this opening, with lumen positioned between the sclera and the choroid. This injection of about 0.1-0.3 mL is performed by smooth and continuous pressure on the syringe plunger in order to spread it around the injection point. This separates the ciliary body and the choroid from sclera, to increase the pressure difference between the anterior chamber and the supra-choroidal space.

The first scleral flap is then sutured with 2 10.0 nylon sutures. At this stage of surgery the viscoelastic material of the invention is injected under the scleral flap. The conjunctiva is sutured with 2-3 nylon sutures and the viscoelastic material of the invention is injected under the conjunctiva in order to create a large conjunctival bleb. Topical antibiotic and anti-inflammatory drops are prescribed postoperatively for 1 month.

Glaucoma is a chronic disease which consist into a continuous intra-ocular high pressure, generally above 20 mm Hg, which slowly destroys the optic nerve and eventually lead to blindness.

Conventional penetrating and non-penetrating surgeries help to reduce the Intra-Ocular Pressure (IOP), with an average post-operative IOP around 15 mm Hg. However to improve chances for the patient to maintain low IOP over time and avoid the need for additional adjunctive treatments, additional medications or other surgeries, lower post-operative IOP shall be targeted. The advantage of the present surgical method and the above preferred additional step over conventional surgical techniques is to lower the targeted IOP below 15 mm Hg. Injection into the supra-choroidal space (also called sub-scleral space) can lower post-operative IOP by 2 to 5 Hg mm vs target IOP without such additional step.

Figure 6:
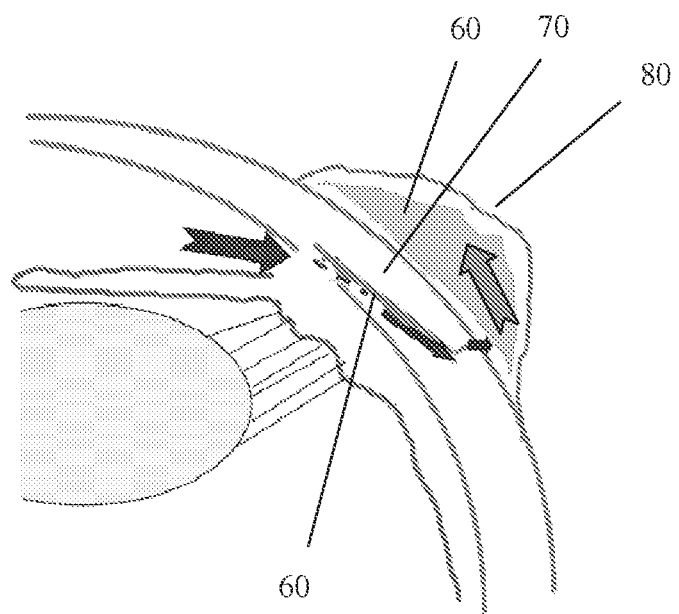
FIG. 6 shows the outflow of the aqueous humor through the filtering bleb until the subconjunctival space filled with cross-linked gel of the invention during perforating surgery.

The trabeculectomy discussed above is an example of perforating surgery. A small incision is made in the conjunctiva, which is then carefully lifted and separated from the sclera, and a half-thickness flap is then dissected up to the edge of the cornea. Then, as is shown in FIG. 6, the viscoelastic material of the invention 60 is injected under the sclera flap 70 as a space maintainer. After the conjunctiva are sutured, the viscoelastic is injected in order to create a large sub-conjunctival bleb 80, as shown on FIG. 8.

Figure 8:
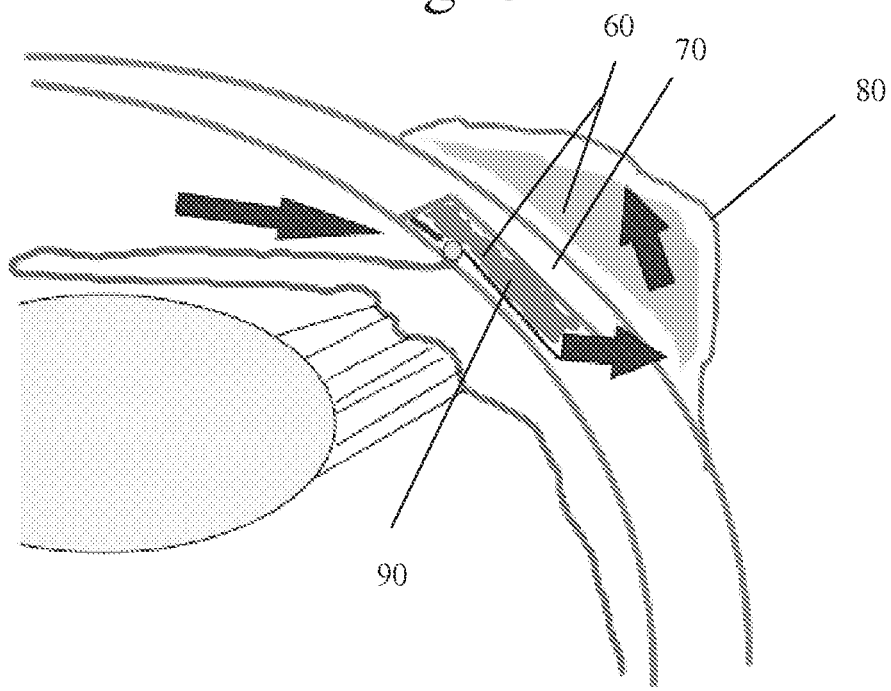
FIG. 8 shows the outflow of the aqueous humor through the filtering bleb through the sclera cavity and until the subconjunctival space filled with cross-linked gel of the invention during non-perforating surgery.

Non-perforating surgery is typified by viscoanalostomy or sclerectomy. As is shown in FIG. 8, injection of the viscoelastic material of the invention 60 is injected into the scleral cavity 90 and under the conjunctiva during non-penetrating surgery in order to create the sub-conjunctival bleb 80.

Figure 9:
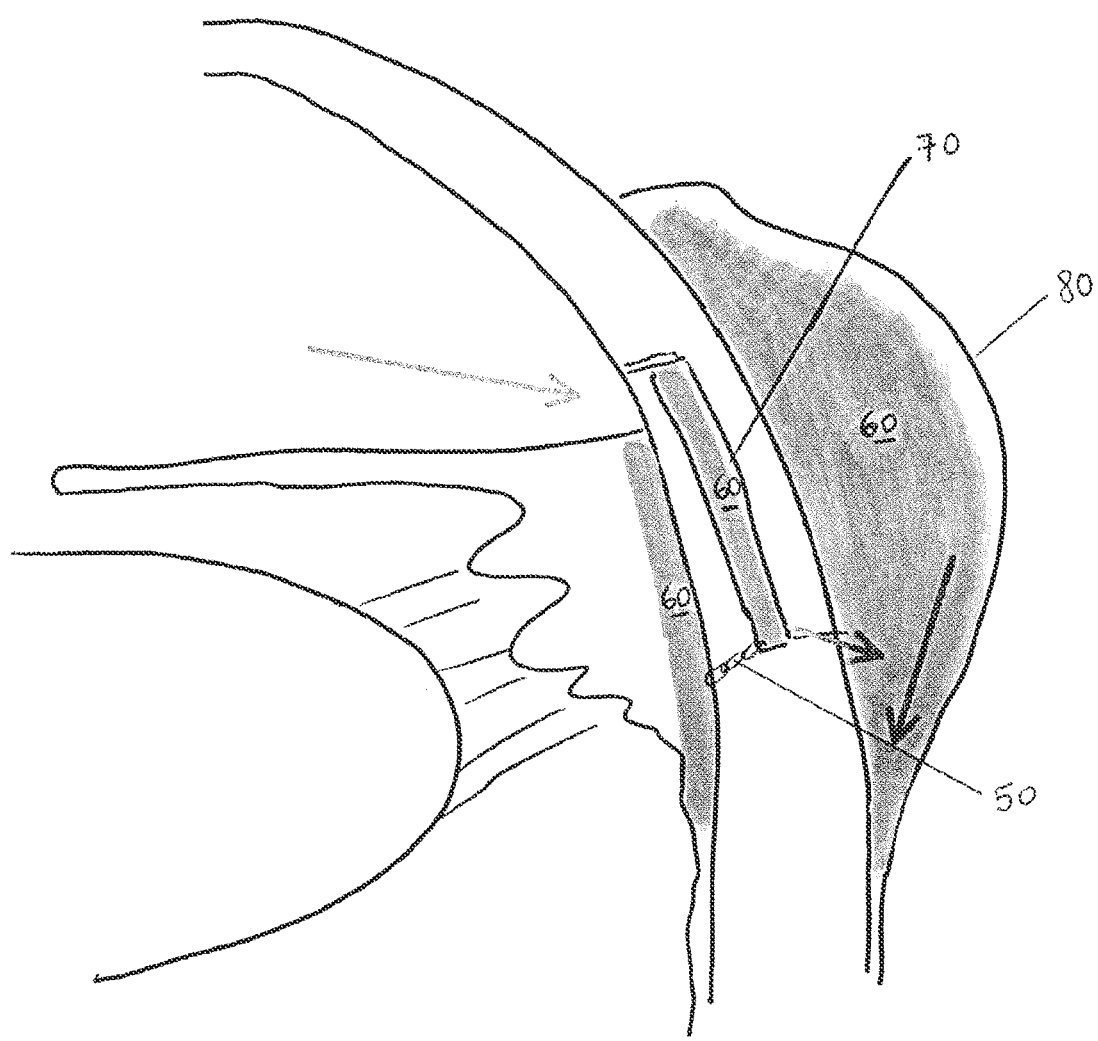
FIG. 9 shows a preferred embodiment of the surgical method with injection of gel into an opening at fornix side of the scleral bed.

According to a preferred embodiment of perforating surgery (trabeculectomy) and non-perforating surgery (viscoanalostomy or sclerectomy) the gel 60 of the present invention is previously injected into an opening 50 made preferably at the fornix side of the scleral bed as shown on FIG. 9.

EXPERIMENTAL

A cross-linked hyaluronic acid (XLHA) was utilized as a space-filling product injected intrasclerally and subconjunctivally during glaucoma surgery.
Patients and Methods:
In a non-randomized pilot study the results of XLHA application during 19 deep sclerectomies (18 patients), 40 viscocanalostomies (33 patients) and 50 trabeculectomies (50 patients), were retrospectively evaluated.

For the deep sclerectomy series the types of glaucoma were primary open angle (POAG) (42%), primary angle closure (PACG) (21%), exfoliative (11%), congenital (16%), traumatic (5%) and ocular hypertension (5%). Most were combined phaco-deep sclerectomies (37%), followed by redo-glaucoma interventions (26%), simple deep sclerectomies (21%) and combined deep sclerectomy-trabeculectomy (16%).

For the viscocanalostomy series the types of glaucoma were exfoliative (43%), POAG (38%), dysgenetique (14%) and PACG (5%). Most were simple viscocanalostomies (76%), followed by combined phaco-viscocanalostomies (15%), combined viscocanalostomy-trabeculectomy (3%), viscocanalostomy-iridectomy (3%) and trabeculectomy (3%). For trabeculectomy series the types of glaucoma were exfoliative (50%), POAG (46%), ICE-syndrome (2%) and Axenfeld-Rieger (2%). Most were simple trabeculectomies (94%) and in 6% combined phaco-trabeculectomy.
Results:
For the deep sclerectomy series the mean pre-operative eye pressure (IOP) was 19.4 mmHg (+−5.2, 12-34) under medical treatment (2.3 anti-glaucoma medication per patient, +−1.4, 0-5). The mean post-operative IOP at the last follow-up was 11.3 mmHg (+−3.6, 6-18) with a mean follow-up of 15.6 weeks (+−40.1, 4-31). One patient was on a pressure reducing medication postoperatively. A diffuse filtration bleb was present in all but one case. Of the 9 eyes that underwent UBM showed a prominent subconjunctival bleb and 5 had an easily visible intrascleral canal.

For the viscocanalostomy series the mean pre-operative IOP was 22.4 mmHg (+−5.7, 14-33) under medical treatment (2.9 anti-glaucoma medication per patient, +−0.7, 1-4). The mean post-operative IOP at the last follow-up was 11.3 mmHg (+−3.3, 4-24) with a mean follow-up of 21.2 weeks (+−49.4, 0.3-90.6). No patient was on a pressure reducing medication postoperatively. A diffuse filtration bleb was present in 87%.

For the trabeculectomy series the mean pre-operative IOP was 22.6 mmHg (+−6.5, 12-40) under medical treatment (2.7 anti-glaucoma medication per patient, +−0.9, 1-4). The mean post-operative eye pressure at the last follow-up was 11.9 mmHg (+−5.1, 2-22) with a mean follow-up of 10.4 weeks (+−5.6, 4-28). One patient was on a pressure reducing medication postoperatively.

DISCUSSION

XLHA is easy to handle and easy to adapt to all surgical procedures. No complication related to the use of XLHA was noticed. Blebs remain calm in most cases, associated with few complications. Postoperative pressure reducing medication was suppressed in all patients but 2.

XLHA seems to be a promising aid in the management of the fibrosis process following deep sclerectomy, viscocanalostomy and trabeculectomy surgery with good IOP control and diffuse blebs with suggested presence of XLHA inside blebs on UBM during the follow up period.

Figure 5:
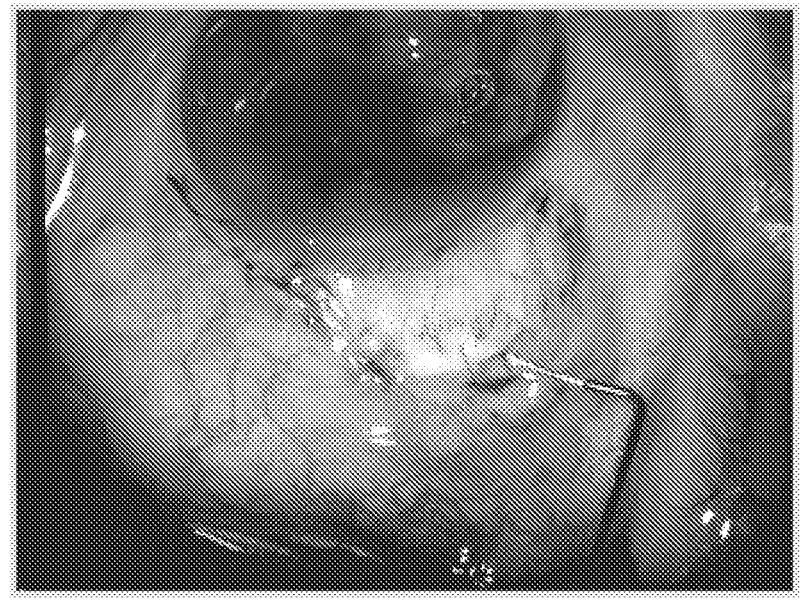
FIG. 5 is a photograph of an eye at the end of non perforating surgery, when the surgeon injects cross-linked gel under the sclera flap.
Figure 7:
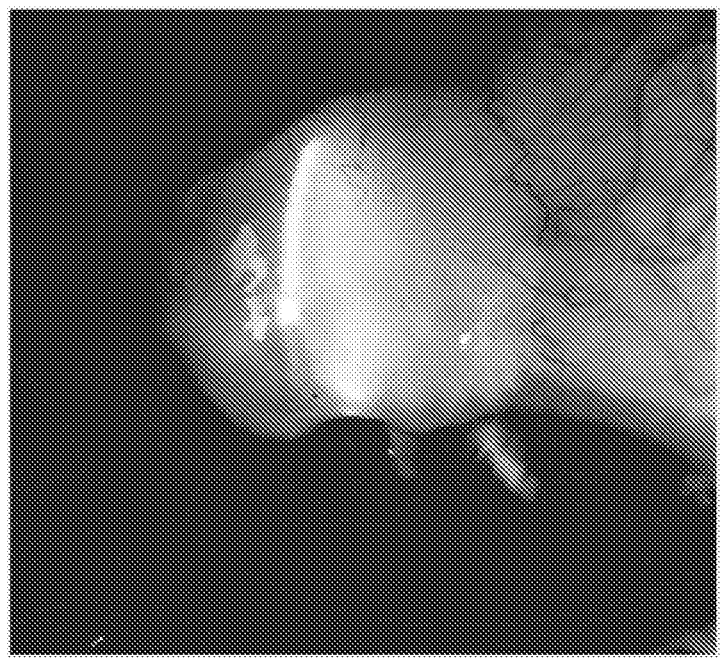
FIG. 7 is a photograph of an eye after glaucoma surgery according to the invention and showing the prominence of the subconjunctival bleb thanks to slit lamp exam.

Additional aspects of the present invention can be observed in FIG. 5, which shows an eye at the end of non perforating surgery, when the surgeon injects cross-linked gel under the sclera flap. FIG. 7 shows an eye after glaucoma surgery according to the invention and showing the prominence of the subconjunctival bleb thanks to slit lamp exam.

In summary, sodium hyaluronate is natural polymer (glycosaminoglycan) obtainable by biofermentation, and is a constituent of all connective tissues of humans and vertebrates. The material is chemically, physically and biologically identical in all species, and has extraordinarily good biological compatibility. Cross-linked monophasic gels of this material have been found to be a superior viscoelastic spacer material for eye surgery, especially eye surgery associated with glaucoma.

It is to be understood that the foregoing descriptions and specific embodiments shown herein are merely illustrative of the best mode of the invention and the principles thereof, and that modifications and additions may be easily made by those skilled in the art without departing for the spirit and scope of the invention, which is therefore understood to be limited only by the scope of the appended claims.

The invention claimed is:

1. A method of treating glaucoma or other eye disease in a patient, comprising:
   during eye surgery, injecting an eye of the patient with a cohesive monophasic gel comprising a cross-linked hyaluronic acid or its salt,
   the injection being under a scleral flap and/or conjunctiva of the eye, thereby creating and maintaining a conjunctival bleb, and/or in a supra-scleral space of the eye thereby reducing the intraocular pressure,
   wherein the concentration of the hyaluronic acid in the gel is in a range of 0.1% to 20% by weight,
   wherein the cohesive monophasic gel comprises a cross-linking agent selected from the group consisting of 1,4-butanediol diglycidylether, 1,2,7,8-Diepoxyoctane, divinylsulfone, carbodiimide, 1-ethyl-3-(3-dimethylaminopropyl) carbodiimide and N-cyclohexyl-N-(4-methylmorpholinium) ethyl carbodiimide.

2. The method according to claim 1, wherein the cross-linked salt of hyaluronic acid is sodium hyaluronate.

3. The method according to claim 1, wherein the cohesive monophasic gel comprises about 2.25% (w/w) of the hyaluronic acid or its salt.

4. The method according to claim 1, wherein the cross-linked hyaluronic acid or its salt has a cross linking ratio of about 0.5% to about 50%.

5. The method according to claim 1, wherein the gel is injected under a scleral flap of the patient.

6. The method according to claim 1, wherein the gel is injected under conjunctiva of the patient.

7. The method according to claim 1, wherein the gel is injected in a supra-scleral space of the patient.

8. The method according to claim 1, wherein the eye surgery comprises performing a trabeculectomy on the patient.

9. The method according to claim 8, wherein the trabeculectomy comprises:
   applying peribulbar anesthesia;
   dissecting the conjunctiva;
   dissecting a scleral flap;
   performing an opening to the anterior chamber of the eye;
   performing an iridectomy;
   creating an opening in the sclera bed, preferably at the fornix side of the scleral bed;
   injecting the gel through the opening in the supra-choroidal (sub-scleral) space;
   suturing the scleral flap;
   injecting the gel under the scleral flap;
   injecting the gel under the conjunctiva; and
   suturing the conjunctiva.

10. The method according to claim 1, wherein the method eye surgery comprises performing a viscocanalostomy performed on the patient.

11. The method according to claim 10, wherein the viscocanalostomy comprises:
   applying peribulbar or topical anesthesia;
   dissecting the conjunctiva
   dissecting a first scleral flap at a site with at least one apparent collecting channel;
   dissecting a second scleral flap close to a ciliary body;
   creating a Trabeculo-Descemet-Membrane window;
   unroofing a Schlemms' canal;
   excising the second sclera flap;
   inserting a canula into two ostia of the Schlemms' canal;
   repeatedly injecting the gel into the two ostia;
   creating an opening in the sclera bed, preferably at the fornix side of the scleral bed;
   injecting the gel through the opening in the supra-scleral space;
   suturing the first scleral flap;
   injecting the gel below the first scleral flap;
   injecting the gel under the conjunctiva to create a large conjunctival bleb; and
   suturing the conjunctiva.

12. The method according to claim 1, wherein the method eye surgery comprises performing a deep sclerectomy performed on the patient.

13. The method according to claim 12, wherein the deep sclerectomy comprises:
   applying peribulbar or topical anesthesia;
   dissecting the conjunctiva
   dissecting a first scleral flap at a site with at least one apparent collecting channel;
   dissecting a second scleral flap close to a ciliary body;
   creating a Trabeculo-Descemet-Membrane window;
   when reaching the Schlemm's canal, unroofing it;
   excising the second scleral flap;
   creating an opening in the sclera bed, at the fornix side of the scleral bed;
   injecting the gel through said opening, in the supra-choroidal (sub-scleral) space;
   suturing the first scleral flap;
   injecting the gel below the first scleral flap;
   injecting the gel under the conjunctiva to create a large conjunctival bleb; and
   suturing the conjunctiva.

14. The method according to claim 1, wherein the eye surgery is glaucoma surgery.

15. A method of treating glaucoma or other eye disease in a patient, comprising:
   during eye surgery, injecting the eye of the patient with a cohesive monophasic hydrogel comprising a cross-linked hyaluronic acid or its salt,
   the injection being under a scleral flap and/or conjunctiva of the eye, thereby creating and maintaining a conjunctival bleb, and/or in a supra-choroidal (sub-scleral) space of the eye thereby reducing the intraocular pressure,
   wherein the concentration of the hyaluronic acid or its salt in the hydrogel is in a range of 1.5% to 3% by weight, and
   the cross-linked hyaluronic acid or its salt has a cross linking ratio of 2% to 20%.

16. The method according to claim 15, wherein the concentration of the hyaluronic acid or its salt in the hydrogel is about 2.25% and the cross linking ratio is about 5%.

* * * * *